US00PP32542P2

(12) United States Plant Patent
Sienicki

(10) Patent No.: US PP32,542 P2
(45) Date of Patent: Dec. 1, 2020

(54) ***ACER* TREE NAMED 'VOLCANO'**

(50) Latin Name: *Acer truncatum*
Varietal Denomination: Volcano

(71) Applicant: Andrzej Sienicki, Wolomin (PL)

(72) Inventor: Andrzej Sienicki, Wolomin (PL)

( * ) Notice: Subject to any disclaimer, the term of this patent is extended or adjusted under 35 U.S.C. 154(b) by 0 days.

(21) Appl. No.: 16/873,380

(22) Filed: Apr. 1, 2020

(51) Int. Cl.
*A01H 5/00* (2018.01)
*A01H 6/00* (2018.01)

(52) U.S. Cl.
USPC ..... Plt./224

(58) Field of Classification Search
USPC ..... Plt./224
CPC ... A01H 5/00; A01H 5/04; A01H 5/12; A01H 5/02; A01H 5/08
See application file for complete search history.

*Primary Examiner* — June Hwu
(74) *Attorney, Agent, or Firm* — Penny J. Aguirre

(57) ABSTRACT

A new cultivar of *Acer truncatum* tree named 'Volcano' that is characterized by its compact growth habit reaching about 3 m in height, its broad obovate to rounded plant shape, its young foliage that is reddish pink in color with yellow veins, and its mature foliage that is gradually changes to all yellow-green in color.

2 Drawing Sheets

Botanical classification: *Acer truncatum.*
Variety denomination: 'Volcano'.

CROSS REFERENCE TO A RELATED APPLICATION

This application is related to a European plant breeders' rights application filed on Jan. 21, 2019, application No. 2019/0192. There have been no offers for sale anywhere in the world prior to the effective filing date of this Application and no accessibility to one of ordinary skill in the art could have been derived from the printed plant breeder's rights documents.

BACKGROUND OF THE INVENTION

The present invention relates to a new and distinct cultivar of *Acer truncatum*, and will be referred to hereafter by its cultivar name, 'Volcano'. 'Volcano' is a deciduous tree grown for use as a landscape plant.

The new cultivar was discovered in June of 2009 as a seedling that arose from seed planted from open pollination of an unnamed and unpatented proprietary plant of *Acer truncatum* from the Inventor's breeding program in Wolomin, Poland. The male parent is unknown.

Asexual propagation of the new cultivar was first accomplished by grafting onto *Acer truncatum* rootstock by the Inventor in Wolomin, Poland in June of 2014. Asexual propagation by grafting has determined that the characteristics of the new cultivar are stable and are reproduced true to type in successive generations.

SUMMARY OF THE INVENTION

The following traits have been repeatedly observed and represent the characteristics of the new cultivar. These attributes in combination distinguish 'Volcano' as a new and unique cultivar of *Acer.*

1. 'Volcano' exhibits a compact growth habit reaching about 3 m in height.

2. 'Volcano' exhibits a broad obovate to rounded plant shape.
3. 'Volcano' exhibits young foliage that is reddish pink in color with yellow veins.
4. 'Volcano' exhibits mature foliage that is gradually changes to all yellow-green in color.

The female parent plant of 'Volcano' differs in having a less compact growth habit, young leaves that are green and only occasionally slightly pink and mature leaves that are dark green with lighter green veins. 'Volcano' can be compared to the *Acer* cultivars 'Aureum' (not patented) and 'Munn001' (U.S. Plant Pat. No. 16,718). 'Aureum' is similar to 'Volcano' in general leaf shape and having colorful foliage. 'Aureum' differs from 'Volcano' in having a considerably more vigorous plant habit, young leaves that are purplish red in color, and mature leaves that are yellow in color. 'Munn001' is similar to 'Volcano' in having a compact plant habit. 'Munn001' differs from 'Volcano' in having leaves with more lobes, young leaves that are red in color, and mature leaves that are yellow in color.

STATEMENT REGARDING PRIOR DISCLOSURES BY THE INVENTOR

The Applicant asserts that no publications or advertisements relating to sales, offers for sale, or public distribution occurred more than one year prior to the effective filing date of this application. Any information about the claimed plant would have been obtained from a direct or indirect disclosure from the Inventor. The Applicant claims a prior art exemption under 35 U.S.C. 102(b)(1) for disclosure and/or sales prior to the filing date but less than one year prior to the effective filing date. Disclosure incudes but may not be limited to a website listing by Van Vliet New Plants.

BRIEF DESCRIPTION OF THE DRAWINGS

The accompanying colored photographs illustrate the overall appearance and distinct characteristics of a 14-month-old tree of the new cultivar as grown in a cold greenhouse in a 15-cm container in Hazerswoude-Dorp, The Netherlands.

Figure 1:
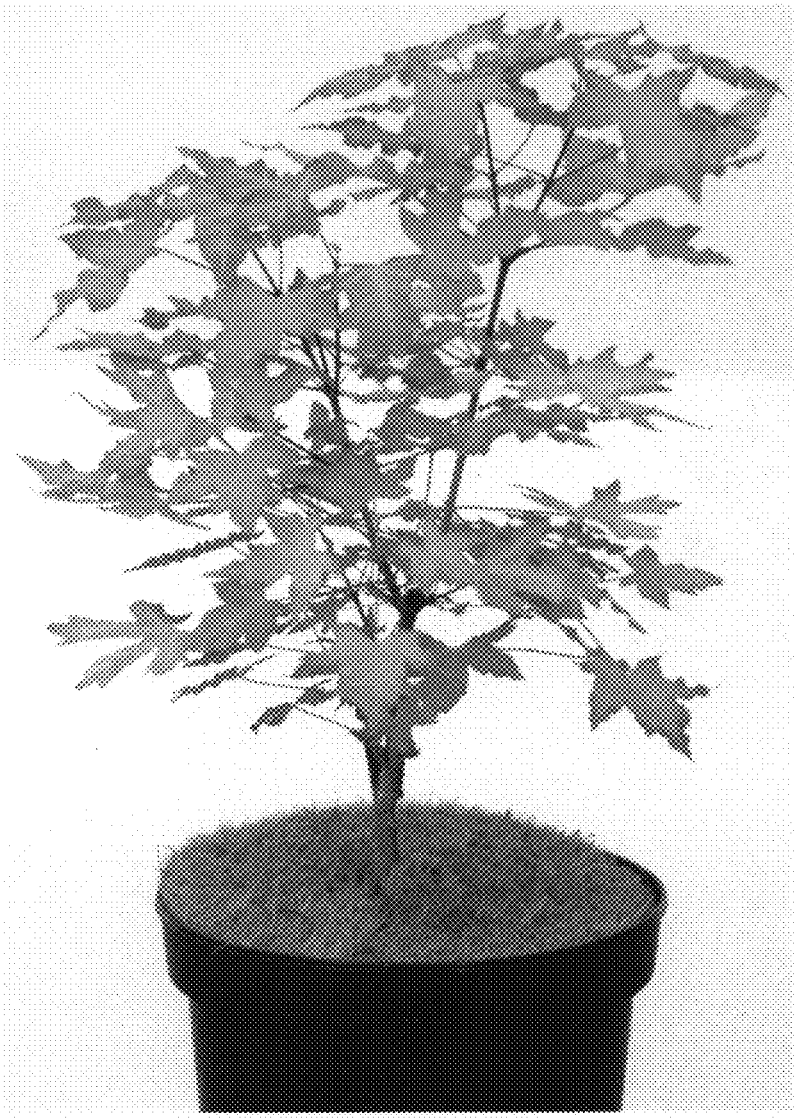
FIG. 1 provides an overall view of the foliage and plant habit of 'Volcano'.
Figure 2:
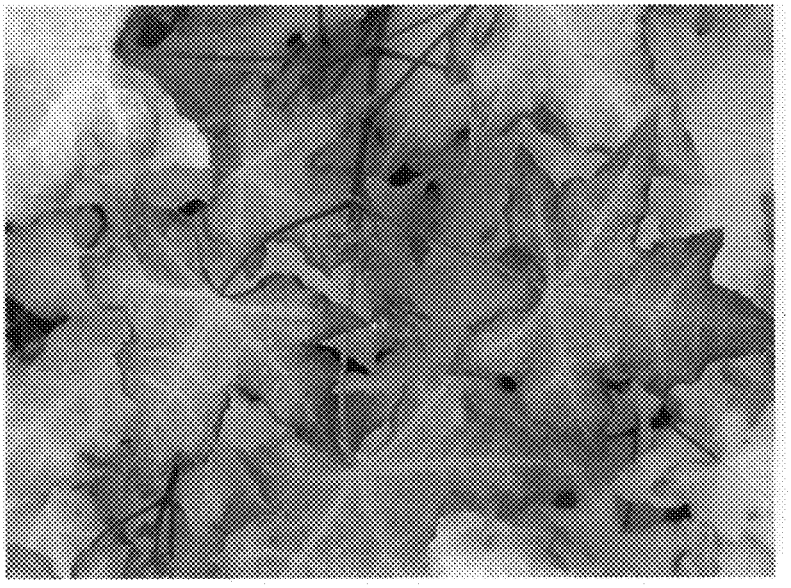

The photograph in FIG. 2 provides a close-up view of the young foliage of 'Volcano'.

Figure 3:
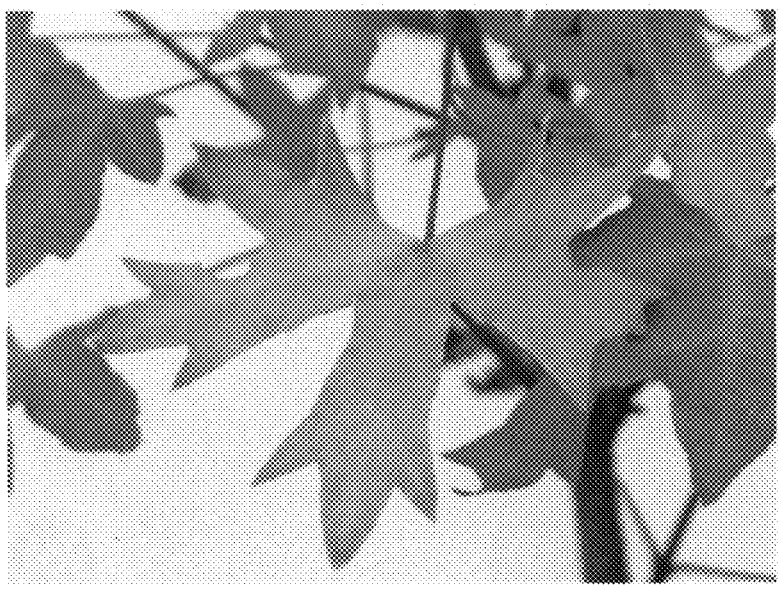

The photograph in FIG. 3 provides a close-up view of the mature leaves of 'Volcano'.

The colors in the photographs may differ slightly from the color values cited in the detailed botanical description, which accurately describe the colors of the new *Acer*.

DETAILED BOTANICAL DESCRIPTION

The following is a detailed description of 14-month-old trees of the new cultivar as grown in a cold greenhouse in 15-cm containers in April in Hazerswoude-Dorp, The Netherlands. The phenotype of the new cultivar may vary with variations in environmental, climatic, and cultural conditions, as it has not been tested under all possible environmental conditions. The color determination is in accordance with The 2015 Colour Chart of The Royal Horticultural Society, London, England, except where general color terms of ordinary dictionary significance are used.

General description:

*Plant type*.—Deciduous tree.

*Plant habit*.—Compact with an obovate to rounded plant shape.

*Height and spread*.—An average of 31 cm in height and 25.8 cm in spread as a 14-month-old tree and reaches about 3 m in height and 2.5 m in spread as a mature plant in the landscape.

*Cold hardiness*.—At least to U.S.D.A. Zone 5.

*Diseases and pests*.—No susceptibility or resistance to diseases or pest has been observed.

*Root description*.—Fibrous, freely branched.

*Propagation*.—Grafting.

*Root development*.—An average of 14 months from a graft to a small marketable plant.

*Growth rate*.—Moderately vigorous.

Branch description:

*Stem shape*.—Round.

*Stem size*.—Main stem; an average of 2 cm in diameter at soil level, lateral branches; an average of 8.8 cm in length and 2 mm in diameter.

*Stem surface*.—Slightly glossy.

*Stem color*.—Young; 178B, mature; 144B, older stems; 199B to 199C.

*Stem strength*.—Strong.

*Stem aspect*.—An average angle of 25° to vertical.

*Internode length*.—An average of 2.6 cm.

*Branching*.—Well-branched, 1 main stem and 8 secondary branches per main branch.

Foliage description:

*Leaf shape*.—Palmately lobed, reniform to orbicular in outline.

*Leaf division*.—Simple.

*Leaf base*.—Truncate.

*Leaf apex*.—Acute, outer tip mucronate.

*Leaf fragrance*.—None.

*Leaf venation*.—Palmate, young leaves upper surface color is 149B, lower surface color is 145A, mature upper surface color is 146C to 146D, lower surface color is 147D.

*Leaf quantity*.—An average of 8 (4 pairs) per lateral branch.

*Leaf margins*.—Palmately 5-lobed, lobe margins serrate with 1 to 2 teeth per lobe, sinus depth deep, sinus orientation is convergent.

*Leaf arrangement*.—Opposite.

*Leaf aspect*.—Flat, leaves in an average angle of 80° to lateral branch.

*Leaf attachment*.—Petiolate.

*Leaf surface*.—Texture of both surfaces glabrous and smooth, upper surface luster matte, lower surface luster moderately glossy.

*Leaf size*.—Average of 6.8 cm in length and 7.9 cm width.

*Leaf color*.—Young leaves upper surface; 145A, leaf tinged towards the margins with 179B, young leaves lower surface; 152D, towards the margins 165B to 165C and 166C to 166D, mature leaves upper surface; 144C, around veins 154D, mature lower surface; 145B to 145C, fall color; both surfaces similar to mature foliage with some tinging of the 179B on the upper surface and 165B on the lower surface.

*Petioles*.—Average of 4.7 cm in length and 1 mm in diameter, texture is smooth and glabrous, glossy luster, strong, upper surface side color 180A, changing to 179B to 179C at the distal end, lower surface side color 179B, changing to 150B to 150C at the distal end, 145A proximal end.

*Stipules*.—None.

Inflorescence description: None observed to date.

Fruit and seed: None observed to date.

It is claimed:

1. A new and distinct cultivar of *Acer truncatum* tree named 'Volcano' as herein illustrated and described.

* * * * *